US010588279B2

(12) United States Patent
Crotteau

(10) Patent No.: US 10,588,279 B2
(45) Date of Patent: Mar. 17, 2020

(54) PROCESS AND METHOD FOR STILLAGE FERMENTATION

(71) Applicant: BIOPROCESS ALGAE LLC, Omaha, NE (US)

(72) Inventor: Adam Crotteau, Lincoln, NE (US)

(73) Assignee: BIOPROCESS ALGAE LLC, Omaha, NE (US)

( * ) Notice: Subject to any disclaimer, the term of this patent is extended or adjusted under 35 U.S.C. 154(b) by 108 days.

(21) Appl. No.: 15/491,498

(22) Filed: Apr. 19, 2017

(65) Prior Publication Data

US 2017/0305767 A1    Oct. 26, 2017

Related U.S. Application Data

(60) Provisional application No. 62/324,951, filed on Apr. 20, 2016.

(51) Int. Cl.
| | |
|---|---|
| A01G 33/00 | (2006.01) |
| C11B 13/00 | (2006.01) |
| A23K 10/38 | (2016.01) |
| A23K 10/16 | (2016.01) |
| A23K 10/37 | (2016.01) |
| C02F 9/00 | (2006.01) |
| A23K 10/12 | (2016.01) |
| C02F 1/04 | (2006.01) |
| C02F 1/38 | (2006.01) |
| C02F 101/32 | (2006.01) |
| C02F 103/32 | (2006.01) |
| C02F 1/00 | (2006.01) |
| C02F 3/32 | (2006.01) |

(52) U.S. Cl.
CPC .............. *A01G 33/00* (2013.01); *A23K 10/12* (2016.05); *A23K 10/16* (2016.05); *A23K 10/37* (2016.05); *A23K 10/38* (2016.05); *C02F 9/00* (2013.01); *C11B 13/00* (2013.01); *C02F 1/04* (2013.01); *C02F 1/38* (2013.01); *C02F 3/322* (2013.01); *C02F 2001/007* (2013.01); *C02F 2101/32* (2013.01); *C02F 2103/32* (2013.01); *C02F 2209/40* (2013.01); *C02F 2305/12* (2013.01); *Y02A 40/88* (2018.01); *Y02P 60/873* (2015.11); *Y02P 60/877* (2015.11); *Y02W 10/30* (2015.05); *Y02W 30/74* (2015.05)

(58) Field of Classification Search
None
See application file for complete search history.

(56) References Cited

U.S. PATENT DOCUMENTS

| | | | |
|---|---|---|---|
| 7,449,313 B2 | 11/2008 | Rush | |
| 7,514,247 B2 | 4/2009 | Rush | |
| 7,662,617 B2 | 2/2010 | Rush | |
| 8,388,846 B2 * | 3/2013 | Chew | C12N 1/06 210/634 |
| 8,481,295 B2 | 7/2013 | Leeuwen et al. | |
| 8,722,911 B2 * | 5/2014 | Bleyer | B01D 3/14 554/8 |
| 9,029,126 B2 | 5/2015 | Bleyer et al. | |
| 9,079,786 B2 | 7/2015 | Leeuwen et al. | |
| 2014/0171670 A1 | 6/2014 | Jenkins et al. | |
| 2015/0305370 A1 | 10/2015 | Bleyer et al. | |

OTHER PUBLICATIONS

Demirbas, A. et al., Energy Conver. Manage. 2011, vol. 52, pp. 163-170.*
Li, H. et al., Biotechnol. Bioeng. 2007, vol. 98, pp. 764-771.*
Alabi et al., Jan. 2009, Microalgae Technologies & Processes for Biofuels/Bioenergy Production in British Columbia: Current Technology, Suitability & Barriers to Implementation, Seed Science, 88 pages.
Ehimen et al., Dec. 2009, Energy recovery from lipid extracted, transesterified and glycerol codigested microalgae biomass, Global Change Biology Bioenergy, vol. 1, Issue No. 6, 10 pages.
Gyenge et al., Jun. 2013, Efficiency of biogas production from corn bioethanol by-products using different inocula, Conference: Energy (IYCE) 2013 4th International Youth Conference on Energy, 7 pages.

* cited by examiner

*Primary Examiner* — Heidi Reese
(74) *Attorney, Agent, or Firm* — Daniel J. Honz; Advent, LLP

(57) ABSTRACT

The present invention generally relates to a novel process in which thin stillage is processed to produce algae oil and protein rich biomass as well as other energy rich byproducts. In accordance with a preferred embodiment, thin stillage is removed from an evaporator during the evaporation process to produce mid-stillage. This mid-stillage is preferably routed to a new process where it is directed to a pretreatment centrifuge to remove suspended solids, sludge and corn oil. Thereafter, the mid-stillage is preferably cooled and then directed to a fermentation tank where the mid-stillage is subject to a batch fermentation process with algae "seed" fed from an algae inoculation system. Once the batch is harvested, the oil-rich algae/mid-stillage is then preferably heated to rupture the cells and liberate the oil. Thereafter, the oil-rich algae/mid-stillage is preferably processed by a centrifuge which produces solids, a light phase oil and a "clean" mid-stillage stream that can be evaporated to a very high level of solids.

13 Claims, 3 Drawing Sheets

PROCESS AND METHOD FOR STILLAGE FERMENTATION

RELATED APPLICATIONS

The present application claims priority to U.S. Provisional Application No. 62/324,951 filed Apr. 20, 2016.

FIELD OF THE INVENTION

The present invention generally relates to a process and method for distilling ethanol and, in particular, to a process and method for increasing the efficiency of thin stillage processing.

BACKGROUND OF THE INVENTION

With reference to FIG. 1, a fuel grade ethanol production process 100 typically includes the steps of milling, saccharification, fermentation, distillation and evaporation (see for example U.S. Pat. No. 7,572,353 to Griend). As shown in FIG. 1, the typical process generally begins by milling grains and combining the milled grains with water and enzymes to break down the grains to produce sugars (saccharification). The mixture is then typically combined with yeast and allowed to ferment.

In the fermentation portion of a typical process, a slurry of milled corn is fermented to produce a beer having a concentration of ethanol that is generally less than 15% by volume. In the distillation portion of a typical process, the ethanol in the beer is extracted in distillation columns. Distillation columns typically have a multitude of horizontal trays for bringing rising ethanol vapor and descending liquid into contact. In a distillation column, low pressure steam percolates up through the beer as the beer cascades from higher trays to lower trays. As the rising steam heats the beer, the ethanol in the beer evaporates and rises to the top of the column where it exits as a vapor. The remaining water and other grain material in the beer descends to the bottom of the column to exit as "beer bottoms" or "whole stillage." This whole stillage material is typically then separated via whole stillage centrifuges into solids and what is known as "thin stillage." The resulting solids, known typically as Wet Distiller's Grains with Solubles (WDGS) are then typically dried to produce Distiller Dried Grains (DDG) which is a valuable feed ingredient. The thin stillage is then typically reduced via an evaporation process where liquid is boiled away from the thin stillage to produce a syrup which can also be dried in the DDG dryer to further increase the output of the animal feed co-product.

While tried and true, the present methods for producing ethanol leave important oils, biomass and other important by products (such as glycerol) unprocessed. Accordingly, the present invention provides a more efficient process for producing ethanol which includes stillage fermentation.

SUMMARY OF THE DISCLOSURE

To minimize the limitations found in the prior art, and to minimize other limitations that will be apparent upon the reading of the specifications, the preferred embodiment of the present invention provides a novel process in which thin stillage is processed to produce algae oil and protein rich biomass as well as other energy rich byproducts.

In accordance with a preferred embodiment, thin stillage is removed from an evaporator during the evaporation process to produce mid-stillage. This mid-stillage is preferably routed to a new process where it is directed to a pre-treatment centrifuge to remove suspended solids, sludge and corn oil. Thereafter, the mid-stillage is preferably cooled and then directed to a fermentation tank where the mid-stillage is subject to a batch fermentation process with algae "seed" fed from an algae inoculation system. Once the batch is harvested, the oil-rich algae/mid-stillage is then preferably heated to rupture the cells and liberate the oil. Thereafter, the oil-rich algae/mid-stillage is preferably processed by a centrifuge which produces solids, a light phase oil and a "clean" mid-stillage stream that can be evaporated to a very high level of solids.

BRIEF DESCRIPTION OF THE DRAWINGS

Elements in the figures have not necessarily been drawn to scale in order to enhance their clarity and to improve the understanding of the various elements and embodiments of the invention. Furthermore, elements that are known to be common and well understood to those in the industry are not depicted in order to provide a clear view of the various embodiments of the invention. Thus, it should be understood that the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

The present invention is directed to a process and method of producing biofuels and other consumable products from biomass. These biofuels and consumable products may include food, feed, chemicals, fuels (i.e. renewable diesel, ethanol etc.) and the like, which for convenience are collectively referred to hereafter as biofuels. In particular, the invention is directed to processes intended to improve the efficiency of conventional ethanol production methods.

According to a preferred embodiment, enzymes used with the present invention may preferably include enzymes such as glucoamylase as well as other enzymes which may selected. Examples of alternative enzymes include: xylanase, amylase, lactase, diastase, sucrase; maltase; invertase; alpha-glactosidase and the like.

Figure 1:
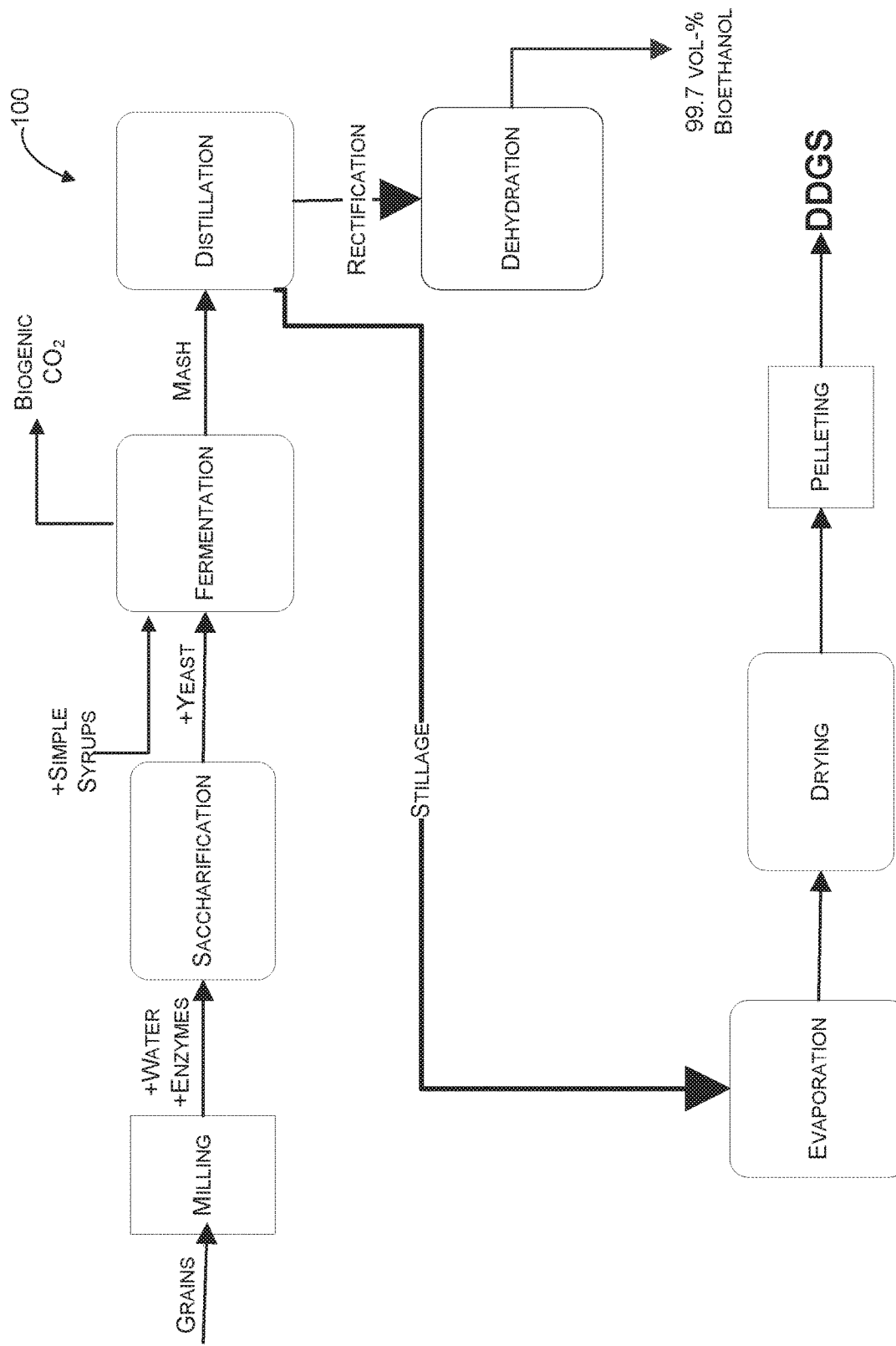
FIG. 1 is a chart illustrating a conventional process for producing ethanol.
Figure 2:
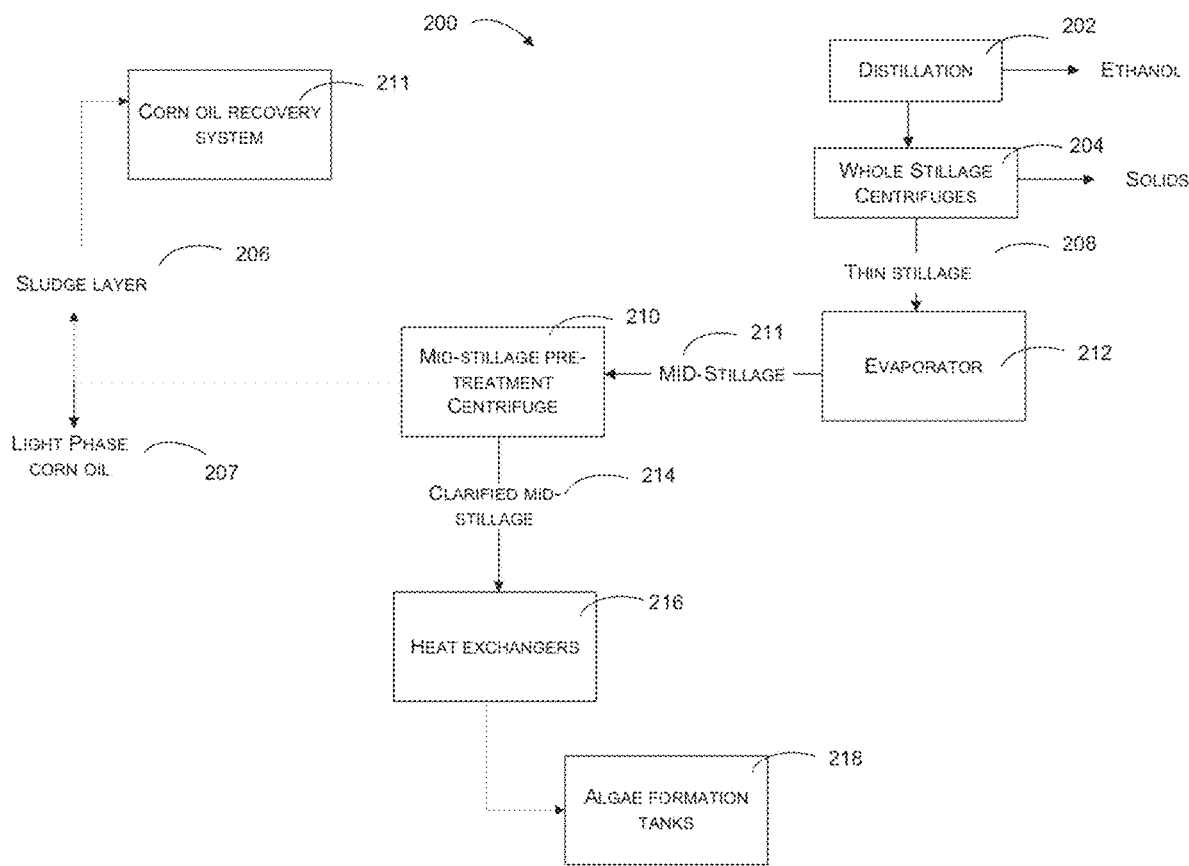
FIG. 2 is a flow chart illustrating an exemplary method for producing biofuels according to a first preferred embodiment of the present invention.

With reference now to FIG. 2, an exemplary preferred embodiment 200 of a process and method in accordance with aspects of the present invention shall now be discussed.

As shown, the exemplary process/method 200 begins at the distillation step 202 of the ethanol production process. As shown, upon distillation 202, ethanol is produced and the remaining whole stillage is processed and sent to a centrifuge 204. At centrifuge 204, the majority of the suspended solids are removed and the remaining "thin stillage" (i.e. solids of 5-8%) are then sent to an evaporator 212 for further processing. At the evaporator, the thin stillage is preferably reduced from 5-8% solids to 13-17% solids before being removed as "mid-stillage" 211 for additional processing. It should be understood that while 13-17% is preferred, the thin stillage may be removed from evaporation at an earlier or later point as desired. Accordingly, the mid-stillage may alternatively contain solids anywhere within the range of 9-27% solids.

Upon removal from the evaporator 212, the mid-stillage 211 preferably is processed by a mid-stillage pre-treatment centrifuge 210 or other mechanical clarification device. At the centrifuge 210, the mid-stillage is preferably separated into light phase corn oil 207, sludge 206 and clarified mid-stillage 214. In accordance with a preferred embodiment, the clarified mid-stillage 214 is in water phase with less than 1% suspended solids. Thereafter, the light phase corn oil 207 is preferably removed and sent to the ethanol plant for further processing. As further shown, the sludge layer 206 is preferably removed with the bulk of the suspended solids from the feed and directed to the corn oil recovery system 211 for further processing.

At a next step, the clarified mid-stillage 214 is preferably then cooled through one or more heat exchangers to cool to fermentation temperature. Generally, the incoming mid-stillage temperature will be 60-85° C. According to a one aspect of the present invention, a first cooling step may be an energy recovery algae process feed/product heat exchanger. In this step, the mid-stillage is preferably cooled by the cold fermentation process product. Thereafter, a second cooling step may preferably be applied in the form of a cooling water heat exchanger. Preferably, the target temperature range from cooling step 2 will be 25-35° C.

Once it reaches the desired temperature, the cooled, clarified mid-stillage 214 is then preferably sent to one or more algae fermentation tanks 218. According to a preferred embodiment, the fermentation tanks 218 are then used to operate a batch fermentation process. According to a preferred embodiment, a strong base (such as sodium hydroxide or the like) is preferably added to the incoming mid-stillage to raise pH from approximately 3.5-4.0 to 5.5-7.0. Further, algae "seed" will preferably be fed from an algae inoculation system to achieve a starting concentration of 1.5-3.0 grams/L algae. Additionally, a large quantity of air will preferably be continuously injected into the fermentation tanks to support the aerobic chemical process with a preferred aeration target of between 0.05-1.00 vvm (ft$^3$/min air/ft$^3$ tank volume). In this process, acid injection or base injection may be added as needed to maintain fermentation tank pH within the target pH range. Further, each fermentation tank will preferably include a dissolved oxygen (DO) probe, temperature transmitter, and foam probe. Preferably, anti-foam chemicals may be used as needed in response to measurements of foam levels. Additionally, each fermentation tank will preferably include a circulation pump which will pump the fermenter contents through an external heat exchanger cooler and assist with providing tank agitation. Still further, each fermentation tank will preferably include a multi-impeller agitator designed to maximize oxygen transfer into the process fluid and a heat exchanger cooler to control temperature in the range of 25-35° C. Preferably, cooling or chilled water will be the cooling source. In accordance with a preferred embodiment, the fermentation batch time may be approximately 48 hours with a possible range of 24-92 hours.

Preferably, the biochemical process in the fermentation tanks will involve algae which will ferment metabolizing the various sources of carbon present in the mid-stillage. According to a further preferred embodiment, any of a variety microalgae species may be used such as algae from the *Chlorella* genus, including *C. protothecoides, C. vulgaris, C. sorokiniana, C. saccharofila*, and other *Chlorella* species. Alternatively, other microalgae species may be used such as *Chlamydomonas reinhardtii, Chlorococcum littorale, Platymonas subcordiformis, Anabaena, Nostoc muscorum, N. spongiaeforme, Westiellopsis prolifica, Oscillotoria Miami BG7* or *Aphanothece halophytico*.

In accordance with a preferred embodiment of the present invention, the ethanol fermentation process of the clarified mid-stillage 214 will produce carbon by-products including: glycerol; organic acids such as acetic and lactic acids; residual sugars such as glucose, maltose and DP3's; residual starches (DP4+): and residual proteins. Preferably, no nitrogen or proteins will be added to the fermentation process in order to maintain a high carbon to nitrogen ratio which will favor algae oil production over protein. Mid-stillage generally contains high levels of minerals needed for algae growth such as Phosphorous and Magnesium. As a result, expensive mineral and chemical additions may be avoided.

Figure 3:
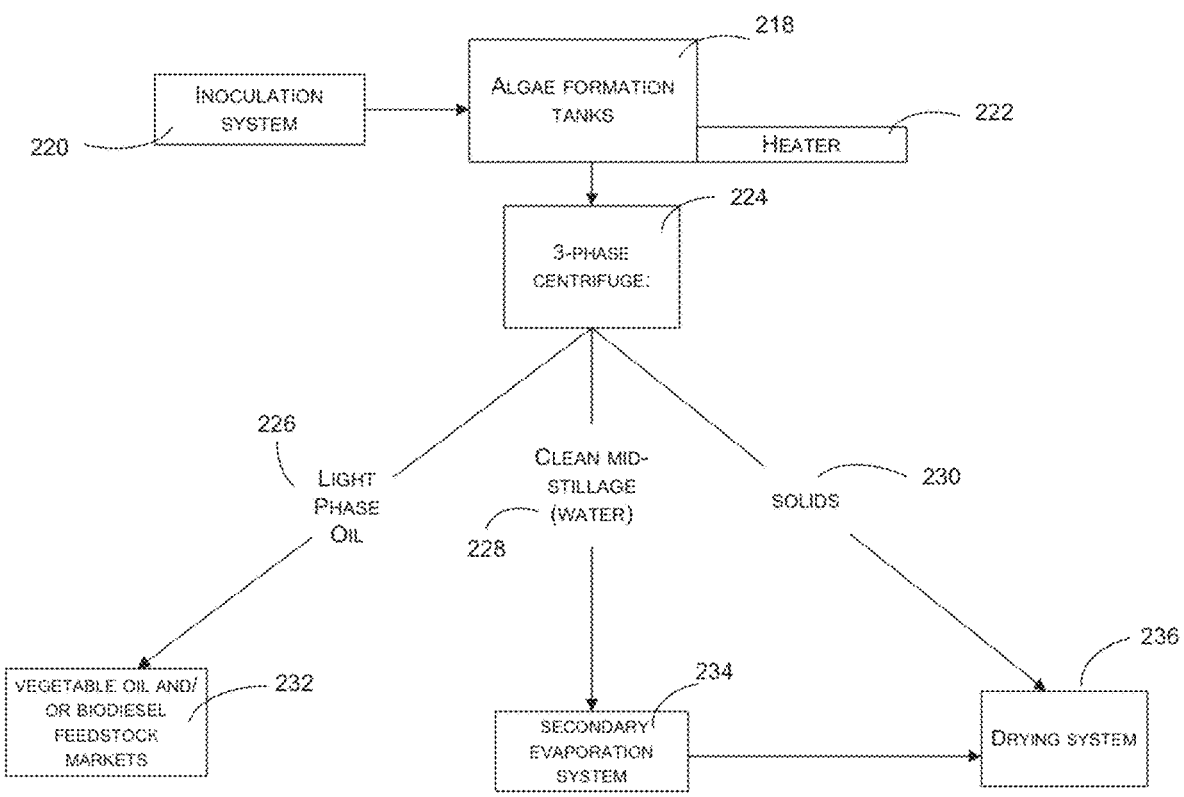
FIG. 3 is a flow chart illustrating an exemplary method for producing biofuels according to a further preferred embodiment of the present invention.

With reference now to FIG. 3, in accordance with a preferred embodiment of the present invention, the algae fermentation system of the present invention will preferably further include an inoculation system 220 to provide a sufficient algae concentration at the start of the fermentation process. Preferably, the inoculation system 220 will be a multi-vessel fermentation system to scale up algae from seed ("test tube") production levels. Preferably, the scale up vessels will share the same features as the full scale fermenters: air injection, cooling, agitation, control of pH and dissolved oxygen.

In accordance with a further aspect of the present invention, the algae inoculation system 220 may preferably use glycerin as an initial carbon source. The use of glycerin will preferably allow the algae to become acclimated to consuming glycerol before the full scale fermentation process begins. According to a preferred embodiment, a potential source of glycerin for the inoculation system may be biodiesel glycerin. According to a further preferred embodiment, glycerin (potentially in the form of biodiesel glycerin) may also be used as possible feedstock for the main algae fermentation system as well.

With reference again to FIG. 3, once the batch formation is completed, the algae/oil-rich mid-stillage is then preferably harvested. In a preferred embodiment, prior to harvesting, the algae/oil-rich mid-stillage is first heated. According to one aspect of the present invention, the algae/oil-rich mid-stillage may preferably be heated first by incoming mid-stillage from evaporation (if available) and then heated to approximately 85-99° C. In accordance with the disclosed process, exposure to high temperatures will cause the algae cells to rupture liberating the algae oil from the cells for recovery by a centrifuge 224.

As further shown in FIG. 3, in accordance with a preferred embodiment, the algae oil is preferably recovered by a 3-phase centrifuge 224 which produces light phase oil 226, clean mid-stillage (primarily water) 228, and sludge/solids 230. As shown, the light phase oil may be separated for sale as vegetable oil and/or biodiesel feedstock 232. As further shown, sludge/solids may be either sent back to the ethanol plant DDGS dryer or dried in a new separate drying system for production of algae protein rich animal feed ingredient.

With respect to the "clean" mid-stillage 228 (water), this liquid is preferably sent to a secondary evaporation system to further reduce the mid-stillage. Preferably, the secondary evaporation product will be fed to the ethanol plant DDGS dryers or other drying system 236.

Applying the principles and features of the present invention, surprising and important efficiencies have been achieved. These efficiencies have been identified and confirmed in multiple test settings. Exemplary test conditions and results are provided as detailed below.

Exemplary Test 1

DATE: Apr. 4, 2017
DESC: M2V11B1B2
GPRE Shenandoah
10L Logs Report
Run Date: 04/12/2017 12:11

Start Details

| Sample Date | Strain | Inoculation source | Inoculated volume L | Dry Weight g/L | Growth Media | Initials |
|---|---|---|---|---|---|---|
| 04/04/2017 11:15 | | M1Y3093-8 | 1,500 | | | NW |

Daily Measurements

| Date and Time | Agitation Speed RPM | Temp ° C. | pH pH | Dissolved Oxygen % | Gas Flow SCFM | Acid mL | Caustic mL | Antifoam mL | Cell Count MCells/mL |
|---|---|---|---|---|---|---|---|---|---|
| 04/04/2017 11:15 | 70 | 27.00 | 0.71 | 50.3 | 0.0 | 450 | 475 | 60 | |
| 04/04/2017 14:45 | 302 | 26.00 | 0.70 | 33.8 | 5.0 | 450 | 475 | 60 | |
| 04/05/2017 00:00 | 420 | 27.40 | 0.70 | 40.0 | 5.0 | 450 | 450 | 60 | |
| 04/05/2017 00:30 | 334 | 23.00 | 0.70 | 42.1 | 5.0 | 450 | 450 | 60 | |
| 04/05/2017 14:00 | 349 | 28.00 | 0.70 | 32.8 | 5.0 | 450 | 450 | 60 | |
| 04/05/2017 17:30 | 335 | 28.00 | 0.70 | 40.2 | 5.0 | 450 | 450 | 60 | |
| 04/06/2017 06:00 | 330 | 28.00 | 0.70 | 33.8 | 5.0 | 450 | 450 | 60 | |
| 04/06/2017 10:00 | 347 | 28.00 | 0.70 | 32.8 | 5.0 | 450 | 450 | 60 | |
| 04/06/2017 14:00 | 378 | 23.00 | 0.70 | 33.7 | 5.0 | 450 | 450 | 50 | |
| 04/06/2017 17:30 | 392 | 23.00 | 0.70 | 39.8 | 5.0 | 450 | 450 | 50 | |
| 04/07/2017 00:00 | 334 | 23.00 | 0.70 | 40.1 | 5.0 | 425 | 450 | 30 | |

HPLC Measurements

| Sample Date | DP4 Wt % | DP3 Wt % | Maltose Wt % | Glucose Wt % | Lactic Acid Wt % | Glycerol Wt % | Acetic Acid Wt % | Ethanol Wt % | Initials |
|---|---|---|---|---|---|---|---|---|---|
| 04/04/2017 11:15 | 0.100 | | 0.256 | 0.103 | | 2.100 | 0.043 | 0.034 | NW |
| 04/04/2017 14:45 | 0.171 | | 0.262 | 0.154 | | 2.183 | | 0.031 | nw |
| 04/05/2017 00:00 | 0.167 | | 0.238 | 0.021 | | 1.007 | 0.007 | 0.027 | ks |
| 04/05/2017 00:30 | 0.164 | | 0.232 | | | 1.700 | | 0.027 | ts |
| 04/05/2017 14:00 | 0.171 | | 0.251 | | | 1.651 | | 0.034 | ts |
| 04/05/2017 17:30 | 0.169 | | 0.252 | | | 1.615 | | 0.034 | ts |
| 04/06/2017 06:00 | 0.169 | | 0.266 | 0.051 | | 1.070 | | 0.023 | ts |
| 04/06/2017 10:00 | 0.162 | | 0.270 | 0.054 | | 1.421 | | 0.022 | nw |
| 04/06/2017 14:00 | 0.100 | | 0.250 | 0.058 | | 1.338 | | 0.022 | nw |
| 04/06/2017 17:30 | 0.172 | | 0.254 | 0.062 | | 1.238 | | 0.021 | nw |
| 04/07/2017 00:00 | 0.107 | | 0.262 | 0.066 | | 0.013 | 0.007 | 0.018 | ts |

| Contaminates Seen | OD540 | Dry Weight g/L | Initials |
|---|---|---|---|
| | 2.0000 | 0.10 | NW |
| | 3.0000 | 1.10 | nw |
| | 8.4000 | 0.70 | ks |
| 3 | 8.8000 | 0.10 | ts |
| 3 | 10.0000 | 4.00 | ts |
| 3 | 10.0000 | 8.10 | ts |
| 3 | 9.4000 | 6.00 | ts |
| 3 | 11.8000 | 0.70 | nw |
| 3 | 13.0000 | 7.20 | ts |
| 3 | 12.8000 | 6.30 | nw |
| | 15.0000 | 7.50 | ts |

Exemplary Test 2

DATE: Mar. 20, 2017
DESC: M7V4B2
GPRE Shenandoah
500L Logs Report
Run Date: 04/12/2017 17:06

Start Details

| Sample Date | Strain | Inoculation source | Inoculated volume L | Dry Weight g/L | Growth Media | Initials |
|---|---|---|---|---|---|---|
| 03/20/2017 13:44 | 4 | see notes | 42,000 | 23.18 | 3 | ks |

Daily Measurements

| Date and Time | Agitation Speed RPM | Temp °C. | pH pH | Dissolved Oxygen % | Gas Flow SCFM | Acid mL | Caustic mL | Antifoam mL | Cell Count MCells/mL |
|---|---|---|---|---|---|---|---|---|---|
| 03/20/2017 14:07 | 45 | 20.30 | 5.57 | 94.0 | 3.0 | 4 | 7 | | 60.00 |
| 03/21/2017 00:00 | 45 | 26.00 | 6.27 | 62.4 | 3.0 | | 7 | | 60.00 |
| 03/21/2017 14:30 | 45 | 26.00 | 6.27 | 37.2 | 3.0 | | 7 | | 140.00 |
| 03/22/2017 00:00 | 45 | 28.70 | 6.40 | 38.7 | 3.0 | 5 | 7 | | 100.00 |
| 03/22/2017 10:00 | 45 | 288.00 | 6.20 | 30.3 | 3.0 | 5 | 7 | | |

HPLC Measurements

| Sample Date | DP4 Wt % | DP3 Wt % | Maltose Wt % | Glucose Wt % | Lactic Acid Wt % | Glycerol Wt % | Acetic Acid Wt % | Ethanol Wt % | Initials |
|---|---|---|---|---|---|---|---|---|---|
| 03/20/2017 14:00 | 1.019 | 0.217 | 0.266 | 0.311 | 0.248 | 1.763 | 5.095 | | ks |
| 03/21/2017 06:00 | 1.577 | 0.181 | | 0.179 | 0.037 | 1.482 | | | nw |
| 03/21/2017 14:00 | 1.521 | | | 0.159 | 0.040 | 1.227 | 0.045 | | ks |
| 03/22/2017 06:00 | 1.320 | | | 0.112 | | | 0.011 | | ks |
| 03/22/2017 10:00 | 1.278 | | 0.032 | 0.088 | 0.002 | | 0.007 | | ts |

| Contaminates Seen | OD540 | Dry Weight g/L | Initials |
|---|---|---|---|
| 3 | 64.6000 | 25.80 | ks |
| 3 | 87.8000 | 29.40 | mw |
| 3 | 112.8000 | 31.20 | ts |
| 3 | 187.0000 | 76.00 | ks |
| | 185.0000 | 51.80 | ts |

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. A process of producing biofuels from biomass following the distillation of biomass, wherein the process comprises the steps of:
   separating ethanol and whole stillage;
   routing the whole stillage to a centrifuge;
   centrifuging the whole stillage to remove solids and to produce a thin stillage, wherein the thin stillage is comprised of 5-8% solids;
   routing the thin stillage to an evaporator;
   evaporating water content from the thin stillage to produce mid-stillage, wherein the mid-stillage is comprised of 9-27% solids;
   separating the mid-stillage into light phase oil, a sludge layer and clarified mid-stillage, wherein the clarified mid-stillage is in water phase with less than 1% suspended solids;
   cooling the clarified mid-stillage;
   routing the clarified mid-stillage to an algae fermentation tank;
   raising the pH of the incoming mid-stillage from approximately 3.5-4.0 to 5.5-7.0;
   adding algae seed from an algae inoculation system to achieve a starting concentration of 1.5-3.0 grams/L algae;
   injecting air into the algae fermentation tank to support an aerobic chemical process;
   maintaining a temperature in the range of 25-35° C.; and
   harvesting oil-rich algae from the algae fermentation tank after a fermentation period.

2. The process of claim 1, wherein the mid-stillage is comprised of 13-17% solids.

3. The process of claim 2, wherein the light phase oil is further processed to produce ethanol.

4. The process of claim 3, wherein the sludge layer is removed and directed to an oil recovery system to produce additional oil.

5. The process of claim 4, wherein the step of cooling the clarified mid-stillage cools the clarified mid-stillage from an incoming temperature of 60-85° C. to a temperature in the range of 25-35° C.

6. The process of claim 5, wherein the step of cooling the clarified mid-stillage is performed using an energy recovery algae process feed/heat exchanger with a cooling stream supplied from the algae fermentation tank.

7. The process of claim 6, wherein the clarified mid-stillage is cooled further in a second cooling step wherein the cooling is applied in the form of a cooling water heat exchanger.

8. The process of claim 7, wherein the seed algae is comprised of one or more algae selected from the group of algae comprising: algae of the *Chlorella* genus, *C. protothecoides, C. vulgaris, C. sorokiniana, C. saccharofila, Chlamydomonas reinhardtii, Chlorococcum littorale, Platymonas subcordiformis, Anabaena, Nostoc muscorum, N. spongiaeforme, Westiellopsis prolifica, Oscillotoria Miami BG7* and *Aphanothece halophytico*.

9. The process of claim 8, wherein the harvesting process comprises the steps of:
heating the oil-rich algae to approximately 85-99° C.;
wherein the step of heating the oil-rich algae comprises a first step of adding heat recovered from incoming mid-stillage.

10. The process of claim 9, wherein algae oil from the oil-rich algae is recovered by a 3-phase centrifuge which produces light phase oil, clean mid-stillage and at least one of sludge or solids.

11. The process of claim 10, wherein the light phase oil is separated as vegetable oil or biodiesel feedstock.

12. The process of claim 11, wherein the at least one of sludge or solids is dried and used for the production of algae protein rich animal feed ingredient.

13. The process of claim 12, wherein the clean mid-stillage is sent to a secondary evaporation system to further reduce the clean mid-stillage, wherein product from the secondary evaporation system is further recovered and dried for use as an animal feed ingredient.

* * * * *